(12) United States Patent
Soll et al.

(10) Patent No.: US 6,991,801 B2
(45) Date of Patent: Jan. 31, 2006

(54) TOPICAL ANTHELMINTIC VETERINARY FORMULATIONS

(75) Inventors: Mark D. Soll, Alpharetta, GA (US); Krishan Kumar, Manalapan, NJ (US); Robert P. Waranis, Armandale, NJ (US); Natalya Shub, Bridgewater, NJ (US)

(73) Assignee: Merial Limited, Duluth, GA (US)

( * ) Notice: Subject to any disclaimer, the term of this patent is extended or adjusted under 35 U.S.C. 154(b) by 0 days.

(21) Appl. No.: 10/818,313

(22) Filed: Apr. 5, 2004

(65) Prior Publication Data

US 2004/0198676 A1    Oct. 7, 2004

Related U.S. Application Data

(60) Provisional application No. 60/460,627, filed on Apr. 4, 2003.

(51) Int. Cl.
*A01N 25/32* (2006.01)

(52) U.S. Cl. .................. 424/406; 424/405; 514/30; 514/248; 514/249; 514/252.05

(58) Field of Classification Search ............... 424/405, 424/406; 514/30, 248, 249, 252.05
See application file for complete search history.

(56) References Cited

U.S. PATENT DOCUMENTS

| 4,468,390 | A | * | 8/1984 | Kitano ................. 514/161 |
| 5,439,924 | A | * | 8/1995 | Miller ................. 514/345 |
| 5,773,422 | A | * | 6/1998 | Komer ................ 514/30 |
| 5,874,103 | A | * | 2/1999 | Moore et al. ........... 424/438 |
| 6,165,987 | A | * | 12/2000 | Harvey ................ 514/30 |
| 6,482,425 | B1 | * | 11/2002 | Huet et al. ............ 424/406 |
| 2003/0055089 | A1 | * | 3/2003 | Sirinyan et al. |
| 2003/0236203 | A1 | * | 12/2003 | Freehauf et al. ........ 514/29 |

FOREIGN PATENT DOCUMENTS

GB    222 1621 A  *  2/1990

* cited by examiner

*Primary Examiner*—Neil S. Levy
(74) *Attorney, Agent, or Firm*—Judy Jarecki-Black; Merial Limited; Thomas Kowalski

(57) ABSTRACT

This invention provides for inter alia, topical anthelmintic formulations which comprise a pharmaceutically active combination consisting of at least one macrocyclic compound and at least one compound selected from the group consisting of praziquantel, morantel and pyrantel, which are dissolved in a non-aqueous solvent or solvent mixture and optionally a thickening agent.

6 Claims, No Drawings

TOPICAL ANTHELMINTIC VETERINARY FORMULATIONS

RELATED APPLICATIONS

This application claims priority to U.S. provisional application 60/460,627, filed Apr. 4, 2003, herein incorporated by reference.

FIELD OF THE INVENTION

This invention provides for topical veterinary formulations, such as spot-on and pour-on formulations, which are used in treating, controlling and preventing of endo—and ectoparasite infections in warm-blooded animals or birds, such as horses, cattle, sheep, pigs and household pets. This invention further provides for a method for increasing the bioavailability of an anthelmintic agent contained in the formulation, which is susceptible to first-pass metabolism in a warm-blooded animal or bird. The inventive topical formulations comprise, for example, at least one macrolide anthelmintic compound and a second anthelmintic agent, for example, praziquantel, morantel and/or pyrantel, a non-aqueous solvent, which dissolves both the first anthelmintic agent and the macrolide anthelmintic compound, and a thickening agent. The inventive topical formulations, which contain praziquantel and/or morantel, as the second anthelmintic agent, exhibit improved systemic availability by eliminating the first pass metabolism of this compound and exhibit stability to hydrolysis.

BACKGROUND OF THE INVENTION

Therapeutic agents are administered to animals by a variety of routes. These routes include, for example, oral ingestion, topical application or parental administration. The particular route selected by the practitioner depends upon factors such as the physiochemical properties of the pharmaceutical or therapeutic agent, the condition of the host, and economic factors.

For example, one method of formulating a therapeutic agent for oral, topical, dermal or subdermal administration is to formulate the therapeutic agent as a paste or as an injectable formulation and reference is made to U.S. application Ser. No. 09/504,741, filed Feb. 16, 2000, now pending, entitled IMPROVED PASTE FORMULATIONS or to Ser. No. 09/346,905, filed Jul. 2, 1999, now pending; Ser. No. 09/112,690, filed Jul. 9, 1999, now allowed; and Ser. No. 09/15,277, filed Sep. 14, 1998, now pending, entitled LONG ACTING INJECTABLE FORMULATIONS CONTAINING HYDROGENATED CASTOR OIL, or U.S. application Ser. No. 10/177,822, entitled ANTHELMINTIC ORAL HOMOGENEOUS VETERINARY PASTES, filed Jun. 21, 2002, now pending. Alternatively, it is possible that therapeutic agents may be administered topically as, for example, as spot-on or pour-on formulations and reference is made to U.S. Pat. No. 6,426,333, issued Jul. 30, 2002 and to co-pending application Ser. No. 09/271,470, filed on Mar. 17, 1999, now allowed, entitled SPOT-ON FORMULATIONS FOR COMBATTING PARASITES and Ser. No. 09/450,186, filed on Nov. 29, 1999, now pending, entitled DIRECT POUR-ON ANTIPARASITIC SKIN SOLUTION AND METHODS FOR TREATING, PREVENTING AND CONTROLLING MYASIS. Other spot-on or pour-on formulations are disclosed in copending application U.S. Ser. No. 10/052,597, filed on Jan. 17, 2002, now pending entitled INSECTICIDAL COMBINATION TO CONTROL MAMMAL FLEAS, IN PARTICULAR FLEAS ON CATS AND DOGS. The disclosure of these patent applications as well as the references cited therein and the references cited herein as well as the references cited in the references are expressly incorporated by reference.

An important area in veterinary science is the control of endo—and ectoparasites in warm-blooded animals, such as equine animals and domestic pets, such as cats and dogs. Infections of parasites, including cestodes and nematodes, commonly occur in animals such as horse, donkeys, mules, zebras, dogs and cats. Various classes anthelmintic agents have been developed in the art to control these infections; see, e.g., U.S. Pat. Nos. 3,993,682 and 4,032,655, which disclose phenylguanidines as anthelmintic agents. Further, the art recognizes that it is advantageous to administer combinations of two or more different classes of anthelmintic agents in order to improve the spectrum of activity; see, e.g., product disclosure for RM® Parasiticide-10, an anthelmintic paste comprising febantel and praziquantel.

Macrolide anthelmintic compounds are known in the art for treating endo—and ectoparasite infections in warm-blooded animals and birds. Compounds that belong to this class of agents include the avermectin and milbemycin series of compounds. These compounds are potent antiparasitic agents against a wide range of internal and external parasites. Avermectins and milbemycins share the same common 16-membered macrocyclic lactone ring; however, milbemycins do not possess the disaccharide substituent on the 13-position of the lactone ring. In addition to treating parasitic insects, avermectins and milbemycins are used to treat endoparasites, e.g., round worm infections, in warm-blooded animals.

The avermectin and milbemycin series of compounds either are natural products or are semi-synthetic derivatives. The natural product avermectins are disclosed in U.S. Pat. No. 4,310,519 to Albers-Schonberg, et al., and the 22,23-dihydro avermectin compounds are disclosed in Chabala, et al., U.S. Pat. No. 4,199,569. For a general discussion of avermectins, which include a discussion of their uses in humans and animals, see "Ivermectin and Abamectin," W. C. Campbell, ed., Springer-Verlag, N.Y.(1989). Naturally occurring milbemycins are described in Aoki et al., U.S. Pat. No. 3,950,360 as well as in the various references cited in "The Merck Index" $12^{th}$ ed., S. Budavari, Ed., Merck & Co., Inc. Whitehouse Station, N.J. (1996). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, and 4,920,148. All these documents are herein incorporated by reference.

Avermectins and milbemycins are ineffective against cestodes, such as tapeworms, which also are a common parasite in warm-blooded animals (see, U.S. Pat. No. 6,207,179). Moreover, echinococcus in companion animals is also very important due to the zoonotic potential to cause alveolar hydatid disease in humans. Of particular importance in the industry is the treatment of equine tapeworms, in general, and *Anoplacephala perfoliata*, in particular (see, e.g., U.S. Pat. No. 6,207,179 or U.S. Pat. No. 5,824,653). In order to treat cestode (and trematode) infections in warm-blooded animals, it is known, to administer 2-acyl-4-oxo-pyrazino-isoquinoline derivatives (see, e.g., U.S. Pat. No. 4,001,441, herein incorporated by reference), pyrantel-type compounds or morantel-type compounds to the animal. A compound of that is often used to treat cestode and trematode infections is praziquantel, which has the following structure:

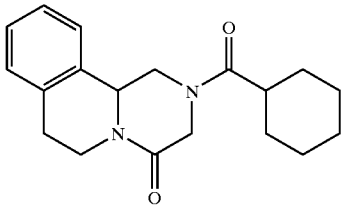

Various methods of formulating antiparasitic formulations are known in the art. These include oral formulations, baits, dietary supplements, powders, shampoos, etc. As mentioned above, often it is beneficial to administer a formulation that contains a combination of two or more anthelmintics, which possess different activity, in order to obtain a composition with a broad-spectrum of activity. Further, the combination allows the user to administer one formulation instead of two or more different formulations to the animal. Formulations which administer a combination of two or more anthelmintics are known in the art. These formulations may be in the form of solutions, suspensions, pastes, oral drenches or pour-on formulations (see, e.g., U.S. Pat. No. 6,165,987 to Harvey or U.S. Pat. No. 6,340,672 to Mihalik). For example, U.S. Pat. No. 4,468,390 to Kitano and U.S. Pat. No. 5,824,653 to Beuvry et al. describe oral anthelmintic compositions for treating nematode and cestode infections in animals, such as horses, that comprise an avermectin or a milbemycin and an isoquinoline compounds, such as praziquantel, to the animal. Similarly, U.S. Pat. No. 6,207,179 to Mihalik describes an oral anthelmintic paste formulations wherein the avermectin or milbemycin is dissolved in an on-aqueous liquid and pyrantel or morantel, compounds which are said in the art to be far less effective in treating tapeworm infections than praziquantel are suspended in the liquid. These prior patents do not describe a formulation wherein the both the praziquantel and the avermectin or milbemycin are dissolved in a solvent and administered to the animal topically. U.S. Pat. No. 6,165,987 describes oral or injectable anthelmintic formulations containing praziquantel and at least one avermectin or milbemycin dissolved in an ester or ester-like compounds, such as glycerol formal, benzyl alcohol and N-methyl-2-pyrrolidone, which may be liquids, pastes or drenches; the amount of praziquantel administered to the animal is always at a dose of more that 2.0 mg per kg of body weight.

Topical formulations for anthelmintic agents are also know in the art. These formulations include compositions for the localized topical applications of antiparasitical formulations, such as spot-on and pour-on solutions. An example of one of these formulations for fipronil is contained in copending application Ser. No. 08/933,016, herein incorporated by reference.

Spot-on formulations are well known techniques for topically delivering an antiparasitic agent to a limited area of the host. For example, U.S. Pat. No. 5,045,536 describes such formulations for ectoparasites. Moreover, it is generally known in the art to formulate avermectin and milbemycin derivatives as spot-on formulations. See, e.g. U.S. Pat. No. 5,045,536; EP 677,054; U.S. Pat. No. 5,733,877; U.S. Pat. No. 5,677,332; U.S. Pat. No. 5,556,868; and U.S. Pat. No. 5,723,488. However, as discussed in U.S. Pat. No. 5,045,536, a large number of solvent systems described in the art provide formulations for localized topical application which cause irritancy or toxicity to the host. Hence, there is a need in the art both for more effect and less irritant or toxic formulations as well as topical formulations which treat both nematode and cestode infections in animals.

U.S. Pat. No. 4,988,696 provides for a method of treating worms in cats by dermally applying praziquantel to the cat. U.S. Pat. No. 6,159,932 provides for topical endoparasiticidal compositions that comprise a macrocyclic lactone with a cyclic desipepside, optionally in the presence of praziquantel or epsiprantel. The inclusion of the praziquantel or epsiprantel is said to increase the action of the cyclic depsipeptides, compounds which are not contemplated by the present invention. U.S. Pat. No. 6,340,672 provides for pour-on parasiticidal formulation comprising, inter alia, praziquantel and avermectin; the formulations comprise a mixture of a pyrrolidone solvent and at least one solvent, such as diethylene glycol monobutyl ether or benzyl benzoate, which is said to form a solvent solution with active agents. The non-aqueous solvent employed in the present invention excludes the presence of solvent mixtures which can contain a pyrrolidone solvent.

SUMMARY OF THE INVENTION

This invention provides for, inter alia, topical formulations consisting essentially of
a) a pharmaceutically active combination consisting of at least one macrocyclic lactone and at least one compound selected from the group consisting of praziquantel, morantel and pyrantel;
b) optionally, a thickening agent;
c) a non-aqueous solvent; and
d) optionally, an antioxidant, a colorant, an acidifying stabilizer, an opacifier, a preservative, a penetration enhancer and a crystallization inhibitor, wherein the pharmaceutically active combination is disclosed in the non-aqueous solvent.

Further, this invention provides for a spot-on and pour-on compositions such as drenches as well as to a method for improving the systemic availability of the second anthelmintic agent, susceptible to first-pass metabolism in the liver, by eliminating the first-pass metabolism of the second agent in an animal which comprises administering a topical formulation to the animal. These and other embodiments are disclosed or are obvious from and encompassed by the following Detailed Description.

In this disclosure and in appended claims, terms such as "comprising", "comprises", "consists essentially of", "consisting essentially of", and the like, have the meanings ascribed to them in U.S. Patent Case Law. The terms "comprises" and "comprising" are open-ended and allow for the inclusion of additional ingredients or steps. The terms "consists essentially of" and "consisting essentially of" are open-ended, but exclude ingredients or steps found in prior art compositions, and ingredients that would effect basic or novel characteristics of the herein invention.

Clearly, a topical formulation, e.g., spot-on, containing or consisting essentially of at least one macrolide, e.g., eprinomectin, ivermectin, moxidectin, doramectin, abamectin, selamectin, advantageously eprinomectin, and a second anthelmentic agent, e.g., praziquantel, morantel, and/or pyrantel, advantageously praziquantel, is a basic or novel feature of the herein invention, as well as methods for preventing or treating parasites on an animal, e.g., dog, cat, by applying the formulation, e.g., monthly, and methods for preparing the formulations, e.g., by administering the ingredients, are also novel and basic features of the invention.

That the invention performs as herein described is surprising, unexpected and nonobvious.

DETAILED DESCRIPTION

This invention provides for topical formulations consisting essentially of
- a) a pharmaceutically active combination consisting of at least one macrocyclic lactone and at least one compound selected from the group consisting of praziquantel, morantel and pyrantel;
- b) optionally, a thickening agent;
- c) a non-aqueous solvent or mixture of solvents; and optionally, an antioxidant, a colorant, an acidifying stabilizer, an opacifier, a preservative, a penetration enhancer and a crystallization inhibitor, wherein the pharmaceutically active combination is dissolved in the non-aqueous solvent or mixture of solvents (e.g., solvent pars) and when the non-aqueous solvent is a solvent mixture, the mixture is not a pyrrolidone solvent. The term "pyrrolidone solvent" includes but is not limited to N-methyl-2-pyrrolidone, 2-pyrrolidone, N,5-dimethyl-2-pyrrolidone, 3,3-dimethyl-2-pyrrolidone, N-ethyl-2-pyrrolidone, N-ethoxy-2-pyrrolidone, N-ethylene-2-pyrrolidone, 1-pyrrolidone, or any combination thereof.

Also provided for are topical formulations comprising:
- a) a pharmaceutically active combination consisting of at least one macrocyclic lactone and at least one compound selected from the group consisting of praziquantel, morantel and pyrantel;
- b) optionally a thickening agent;
- c) a non-aqueous solvent or solvent mixture (e.g., solvent pair) wherein said solvent is selected from the group consisting of propylene glycol, polyethylene glycol, glycerol formal, benzyl alcohol, mixture of glycerides/triglycerides and their derivatives (Miglyol®), a diethylene glycol monoethyl ether (Transcutol®), propylene glycol monolaurate (contains 90% non-esters) (Lauroglycol 90®), dimethylforamide, dimethylsulfoxide, dimethylacetamide, dimethyl isosorbide, apricot kemal oil PEG-6 esters (Labrafil M 1944 CR®, and combination thereof; and
- d) optionally, an antioxidant, a colorant, an acidifying stabilizer, a preservative, opacifier, and/or a crystallization inhibitor wherein the pharmaceutically active combination is dissolved in the non-aqueous solvent or solvent mixture and the formulation does not contain any further pharmaceutically active substances.

Preferred topical formulations are spot-on and pour-on topical formulations; pour on formulations include drenches. Preferred spot-on compositions include a spot-on composition which comprises:
- a) a pharmaceutically active combination consisting of at least one macrocyclic lactone and at least one compound selected from the group consisting of praziquantel, morantel and pyrantel;
- b) a thickening agent; and
- c) a non-aqueous solvent and a spot-on composition which includes
- (1) an effective amount of a combination which comprises a macrocyclic lactone and praziquantel, morantel and/or pyrantel;
- (2) a liquid carrier vehicle comprises a solvent and a cosolvent wherein the solvent is selected from the group consisting of acetone, acetonitrile, benzyl alcohol, butyl diglycol, dimethylacetamide, dimethyl isosorbide dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone, diethylene glycol monoethyl ether, ethylene glycol, diethyl phthalate, $C_8$–$C_{10}$ caprylic/capric triglycerides (Miglyol®), apricot kemal oil PEG-6 esters (Labrafil®), and a mixture of at least two of these solvents and the cosolvent is selected from the group consisting of ethanol, including absolute ethanol, isopropanol or methanol; and
- (3) optionally, a crystallization inhibitor selected from the group consisting of an anionic surfactant, a cationic surfactant, a non-ionic surfactant, an amine salt, an amphoteric surfactant, polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, polyvidone and acrylic derivatives, or a mixture of these crystallization inhibitors.

The inventive topical formulations provide for the combination of at least two different anthelmintic agents, one of which is a macrolide anthelmintic compound. The classes of compounds encompassed by the first agent are well known to practitioners in this art to be useful against endoparasites, such as roundworms and ectoparasites such as flies. Preferred ranges for the amounts of these compounds include from about 0.01 to about 0.5%. The second anthelmintic agents are those which are useful against tapeworms. These compounds include, in addition to praziquantel and its related compounds, anthelmintic agents such as morantel and pyrantel (see, U.K. Patent 1,120,587 for a description of morantel and its preparation and U.S. Pat. No. 3,502,661 for a description of pyrantel and its related compounds). Preferred ranges of amounts for these compounds include from about 1% to about 20%.

The macrolide anthelmintic compounds contemplated in this invention are also well known to a practitioner of this art. These compounds include avermectins and milbemycins, some of which are discussed above. Non-limiting examples of compounds belonging to this class are represented by the following structure:

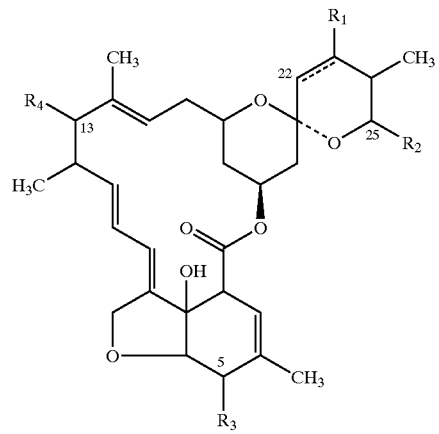

where the broken line indicates a single or a double bond at the 22,23-positions;

$R_1$ is hydrogen or hydroxy provided that $R_1$ is present only when the broken line indicates a single bond;

$R_2$ is alkyl of from 1 to 6 carbon atoms or alkenyl of from 3 to 6 carbon atoms or cycloalkyl of from 3 to 8 carbon atoms;

$R_3$ is hydroxy, methoxy or $=NOR_5$ where $R_5$ is hydrogen or lower alkyl; and $R_4$ is hydrogen, hydroxy or

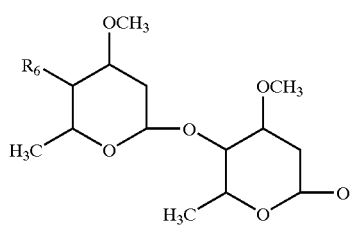

where $R_6$ is hydroxy, amino, mono-or di-lower alkylamino or lower alkanoylamino.

The preferred compounds are avermectin B1a/B1b (abamectin), 22,23-dihydro avermectin B1a/B1b (ivermectin) and the 4"-acetylamino-5-ketoximino derivative of avermectin B1a/B1b. Both abamectin and ivermectin are approved as broad-spectrum antiparasitic agents. The structures of abamectin and ivermectin are as follows:

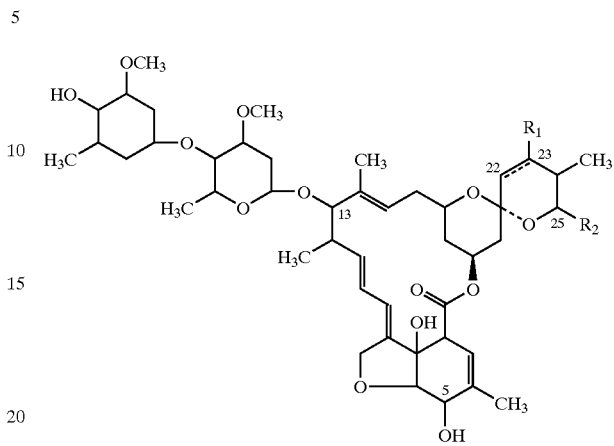

wherein for abamectin the broken line represents a double bond and $R_1$ is not present and for ivermectin the double bond represents a single bond and $R_1$ is hydrogen; and $R_2$ is isopropyl or sec-butyl.

The 4"-acetyl amino-5-ketoximino derivatives of avermectin B1a/B1b has the following structural formula:

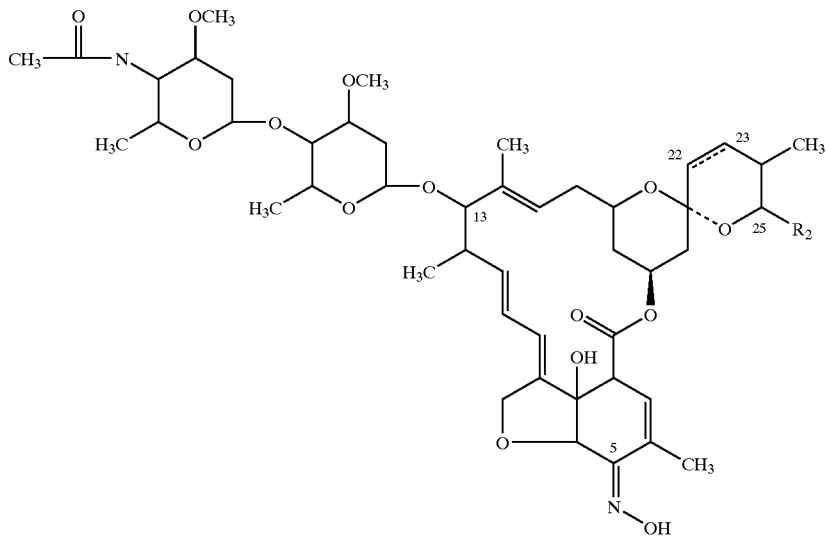

where $R_2$ is isopropyl or sec-butyl.

The avermectin products are generally prepared as a mixture of at least 80% of the compound where $R_2$ is sec-butyl and no more than 20% of the compound where $R_2$ is isopropyl.

Other preferred avermectins include emamectin, eprinomectin, and doramectin. Doramectin is disclosed in U.S.

Pat. No. 5,089,490 and EP 214 738. This compound has the following structure:
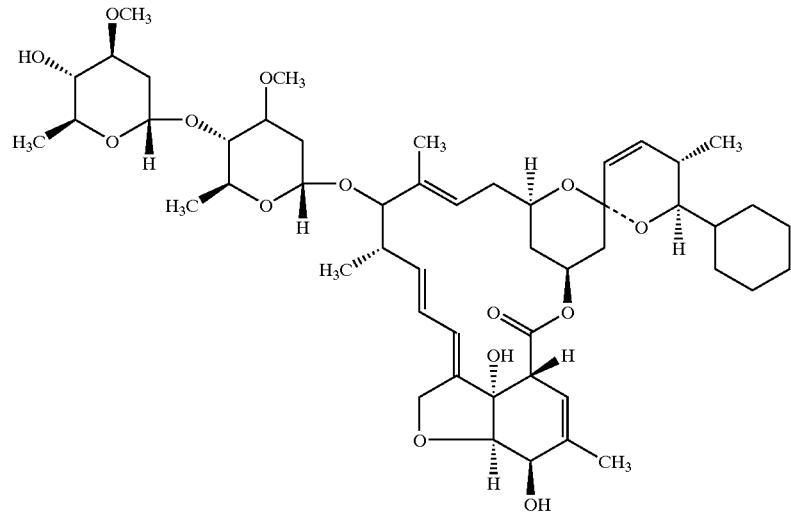
In the present formulations, eprinomectin is especially preferred. This compound has the following structure:
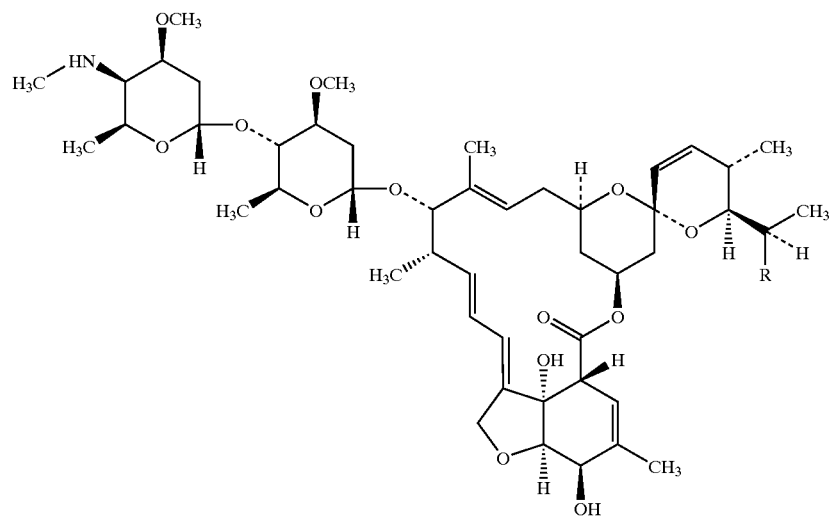
Component B₁ₐ  R = CH₂CH₃
Component B₁ᵦ  R = CH₃

U.S. Pat. No. 4,874,749 discloses this compound and its preparation.

A representative structure for a milbemycin is that for milbemycin $\alpha_1$:

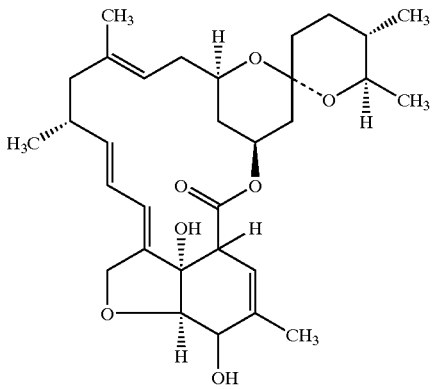

An especially preferred milbemycin is moxidectin, whose structure is as follows:

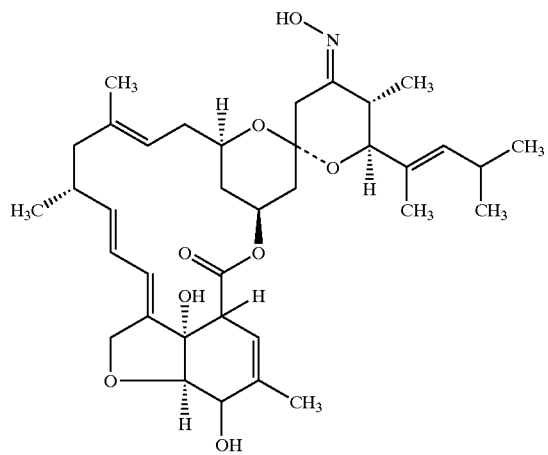

The compound is disclosed in U.S. Pat. No. 5,089,490.

The monosaccharide avermectin derivatives are also preferred especially where an oxime substitution is present on the 5-position of the lactone ring. Such compounds are described, for example, in EP 667,054. Selamectin is an especially preferred compound of this class of derivatives.

This application contemplates all pharmaceutically or veterinary acceptable acid or base salts forms of the anthelmintic compounds, where applicable. The term "acid" contemplates all pharmaceutically or veterinary acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically or veterinary acceptable aliphatic, alicyclic and aromatic carboxylic acids, dicarboxylic acids tricarboxylic acids and fatty acids. Preferred acids are straight chain or branched, saturated or unsaturated $C_1$–$C_{20}$ aliphatic carboxylic acids, which are optionally substituted by halogen or by hydroxyl groups, or $C_6$–$C_{12}$ aromatic carboxylic acids. Examples of such acids are carbonic acid, formic acid, fumaric acid, acetic acid, propionic acid, isopropionic acid, valeric acid, $\alpha$-hydroxy acids, such as glycolic acid and lactic acid, chloroacetic acid, benzoic acid, methane sulfonic acid, and salicylic acid. Examples of dicarboxylic acids include oxalic acid, malic acid, succinic acid, tataric acid and maleic acid. An example of a tricarboxylic acid is citric acid. Fatty acids include all pharmaceutically or veterinary acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

The term "base" contemplates all pharmaceutically or veterinary acceptable inorganic or organic bases. Such bases include, for example, the alkali metal and alkaline earth metal salts, such as the lithium, sodium, potassium, magnesium or calcium salts. Organic bases include the common hydrocarbyl and heterocyclic amine salts, which include, for example, the morpholine and piperidine salts.

The ester and amide derivatives of these compounds, where applicable, are also contemplated. Specific compounds which belong to this class of macrolide antiparasitic agents are well known to the practitioner of this art.

In one embodiment, the solvents provided for in the inventive formulations are those polar solvent that will dissolve both the first anthelmintic agent and the second macrolide anthelmintic compound. These solvents include, for example, glycerol formal, 1-methylpyrrolidone (NMP), propylene, glycol, polyethylene glycol, benzyl alcohol, mixtures of glyceride/triglyceride and their derivatives, such as caprilic/capric acid triglyceride, or fatty acid esters (miglyol products) diethylene glycol monoethyl ether (transcutol®), lauroglycol 90, dimethylfomamide (DMF), dimethyl sulfoxide (DMSO) and mixtures of these solvents. Glycerol formal exists in two isomeric forms, the $\alpha,\alpha'$-form and the $\alpha,\beta$-form. These forms are reproduced below:

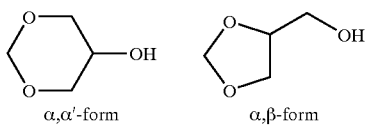

$\alpha,\alpha'$-form       $\alpha,\beta$-form

In other embodiment, a solvent-pair, i.e. a mixture of two solvents one of which dissolves the macrocyclic lactone and the second of which dissolves the antihelmintic agents used to form the solutions. Typical solvents include those mentioned elsewhere in the application. Preferably, solvents that may be used in solvent pairs include isopropyl myristate, isopropanol, propylene glycol, polyethylene glycol, Miglyol$^R$ 840 (propylene glycol dicaprylate/dicaprate [CAS 68 583-51-7]), benzyl alcohol, glycofurol, N,N-dimethylacetamide, dimethyl isosorbide, diethyleneglycol monoethyl ether, and Labrafil$^R$ alcoholysis/esterification products, such as alcoholysis/esterfication product of apricot kemal oil and PEG 300 (Labrafil$^R$ M1944 CS). Especially preferred solvent-pairs include Labrafil$^R$ M1944 CS/isopropanol; propylene glycol/isopropanol/glycerol formal; dimethylacetamide/isopropanol; dimethylacetamide/Miglyol$^R$; isopropanol/dimethyl isosorbide; or Miglyol$^R$/dimethyl isosorbide.

The thickeners contemplated by this invention are well known to a practitioner of this art. Compounds which function as thickeners include, for example, povidone, maltodextrin, polydextrate, EMDEX (dextrates), carboxypolymethylene (Carbomer®), polyethylene glycol and celluloses, such as hydroxypropyl celluloses. An especially preferred thickener is povidone. Thickeners may be present in amounts of from about 0.1% to about 25%.

Opacifiers may be added to absorb and/or reflect certain light and/or energy of certain wavelengths and may thus enhance the stability of the formulations. Opacifiers include, for example, zinc oxide or titanium dioxide and may be present in amounts from about 0.5 to 2.5%. Titanium dioxide is especially preferred. These compounds are well known to practitioners of this art.

Additionally, the inventive formulations may contain other inert ingredients such as antioxidants, preservatives, or pH stabilizers. These compounds are well known in the formulation art. Antioxidant such as an alpha tocopheral, ascorbic acid, ascobyl palmitate, fumeric acid, malic acid, citric acid, sodium ascorbate, sodium metabisulfate, n-propyl gallate, BHA (butylated hydroxyanisole), BHT (butylated hydroxytoluene), monothioglycerol and the like, may be added to the present formulation. The antioxidants are generally added to the formulation in amounts of from about 0.01 to about 2.0%, based upon total weight of the formulation, with about 0.05 to about 1.0% being especially preferred. Preservatives, such as the parabens (methylparaben and/or propylparaben), are suitably used in the formulations in amounts ranging from about 0.01 to about 2.0%, with about 0.05 to about 1.0% being especially preferred. Other preservatives include benzalkonium chloride, benzethonium chloride, benzoic acid, benzyl alcohol, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, sodium benzoate, sodium propionate, sorbic acid, thimerosal, and the like. Preferred ranges for these compounds include from about 0.01 to about 5%.

Colorants may be added to the inventive formulations. Colorants contemplated by the present invention are those commonly known in the art. Specific colorants include, for example, dyes, an aluminum lake, caramel, colorant based upon iron oxide or a mixture of any of the foregoing. Especially preferred are organic dyes and titanium dioxide. Preferred ranges include from about 0.1% to about 25%.

Compounds which acidify the formulation are also contemplated. Again, acidifying compounds and their use to lower the pH of a formulation are well known to a practitioner in the art. Examples of such acidifying stabilizers include, but are not limited to compounds selected from the group consisting of ascorbic acid, malic acid, isoascorbic acid, cysteine hydrochloride, cysteine dihydrochloride, citric acid fumaric acid, acetic acid, sorbic acid, glycine hydrochloride, arginine hydrochloride, succinic hydrochloride, succinic acid, tartaric acid, phosphoric acid, hydrochloric acid, glucono-delta-lactone, and the like. In one embodiment of the present invention, pH ranges for the formulated product, when dispersed in 100 ml of purified water is a pH of from about 4.0 to about 6.5. Chelating agents may include EDTA, diethanolamine and triethanolamine.

The inventive topical formulations may also contain penetration enhancers, such as dimethylacetamide, Transcutol®, DMSO or dimethyl isorbide, or chelating agents. Penetration enhancers are used in small amounts, amounts that are of such quantity that they will not dissolve both actives.

The inventive formulations may be administered to warm-blooded animals and birds. Warm-blooded animals include, for example, all ruminants, equines, canines and felines. Especially preferred are cattle, sheep, pigs, dogs, cats, horses and the like. The amount of each of anthelmintic compounds is well known to a practitioner of this art. Preferred amounts of praziquantel include, for example, from about 0.5 mg/kg to about 10 mg/kg of animal body weight, with a range of about 2 mg/kg or 2.5 mg/kg to about 7.5 mg/kg of body weight being preferred, with 7.5 mg/kg to 10 mg/kg being especially preferred. A most especially preferred amount is about 7.5 mg/kg of animal body weight. Preferred ranges for the anthelmintic macrolide compounds include, for example about 0.01 to about 200 mg/kg of animal body weight, with the ranges of about 0.1 to about 50 mg/kg and from about 1 to about 30 mg/kg being especially preferred.

The topical formulations may be used to treat a number of ecto-and endoparasite infections. The determining of a treatment protocol for an infection of a specific parasite or parasites would be well within the skill level of a practitioner of the veterinary art. This invention further provides for a method to increase the bioavailability of the at least two different anthelmintic agents in the animal.

A preferred spot-on compositions comprises:
(1) a pharmaceutically amount of a combination comprising macrocyclic lactone and praziquantel, morantel and/or pyrantel;
(2) a pharmaceutically or veterinary acceptable liquid carrier vehicle; and
(3) optionally, a crystallization inhibitor More preferably, this invention provides for a spot-on formulation which comprises:
(1) a pharmaceutical combination which consists of an effective amount of a macrocyclic lactone selected from the group consisting of avermectins, ivermectin, abamectin, doramectin, moxidectin, selamectin, milbemycins and their derivatives;
(2) the liquid carrier vehicle comprises a solvent and a cosolvent wherein the solvent is selected from the group consisting of acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone, in particular N-methylpyrrolidone, diethylene glycol monoethyl ether, ethylene glycol, diethyl phthalate fatty acid esters, such as the diethyl ester or diisobutyl adipate, and a mixture of at least two of these solvents and the cosolvent is selected from the group consisting of absolute ethanol, isopropanol or methanol.
(3) a crystallization inhibitor selected from the group consisting of an anionic surfactant, a cationic surfactant, a non-ionic surfactant, an amine salt, an amphoteric surfactant or polyvinylpyrrolidone, polyvinyl alcohols, copolymers of vinyl acetate and vinylpyrrolidone, polyvidone, polyethylene glycols, benzyl alcohol, mannitol, glycerol, sorbitol, polyoxyethylenated sorbitan esters; lecithin, sodium carboxymethylcellulose, and acrylic derivatives, or a mixture of these crystallization inhibitors.

Administration of the inventive formulation may be intermittent in time and may be administered daily, weekly, biweekly, monthly, bimonthly, quarterly, or even for longer durations of time. The time period between treatments depends upon factors such as the parasite(s) being treated, the degree of infestation, the type of mammal or bird and the environment where it resides. It is well within the skill level of the practitioner to determine a specific administration period for a particular situation. This invention contemplates a method for permanently combating a parasite in an environment in which the animal is subjected to strong parasitic pressure where the administration is at a frequency far below a daily administration in this case For example, it is preferable for the treatment according to the invention to be carried out monthly on dogs and on cats.

Spot-on formulations may be prepared by dissolving the active ingredients into the pharmaceutically or veterinary acceptable vehicle. These formulations will vary with regard to the weight of the therapeutic agent in the combination depending on the species of host animal to be treated, the severity and type of infection and the body weight of the host. The compounds may be administered continuously, particularly for prophylaxis, by known methods. Generally, a dose of from about 0.001 to about 10 mg per kg of body weight given as a single dose or in divided doses for a period of from 1 to 5 days will be satisfactory but, of course, there can be instance where higher or lower dosage ranges are indicated and such are within the scope of this invention. It is well within the routine skill of the practitioner to determine a particular dosing regimen for a specific host and parasite. While not wishing to be bound by theory, it is believed that the invention spot-on formulation work by the dose dissolving in the natural oils of the host's skin, fur or feathers. Further as the inventive formulations are not ingested orally, one does not have to be concerned about disguising the taste of the active agents. This is especially important with cats.

The formulations of the present invention provide for the topical administration of a concentrated solution, suspension, microemulsion or emulsion for intermittent application to a spot on the animal, generally between the two shoulders (solution of spot-on type). It has been discovered that the inventive formulations are especially active against parasites when the formulations are applied to mammals and birds, especially poultry, dogs, zebras, cats, sheep, pigs, cattle and horses. The liquid carrier vehicle for the preferred spot-on formulations comprises a pharmaceutically or veterinary acceptable organic solvent and optionally an organic cosolvent.

The organic solvent for the liquid carrier vehicle will preferably have a dielectric constant of between about 10 and about 35, preferably between about 20 and about 30, the content of this solvent in the overall composition preferably representing the remainder to 100% of the composition. It is well within the skill level of the practitioner to select a suitable solvent on the basis of these parameters.

The organic cosolvent for the liquid carrier vehicle will preferably have a boiling point of less than about 100° C., preferably of less than about 80° C., and will have a dielectric constant of between about 10 and about 40, preferably between about 20 and about 30; this cosolvent can advantageously be present in the composition according to a weight/weight (W/W) ratio with respect to the solvent of between about 1/15 and about 1/2; the cosolvent is volatile in order to act in particular as drying promoter and is miscible with water and/or with the solvent. Again, it is well within the skill level of the practitioner to select a suitable solvent on the basis of these parameters.

The organic solvent for the liquid carrier includes the commonly acceptable organic solvents known in the formulation art. These solvents may be found, for example, in Remington Pharmaceutical Science, 16$^{th}$ Edition (1986). These solvents include, for example, ethyl acetate, ethanol, isopropanol, dimethylformamide, dichloromethane or diethylene glycol monoethyl ether (Transcutol®). These solvents can be supplemented by various excipients according to the nature of the desired phases, such as $C_8$–$C_{10}$ caprylic/capric triglyceride (Estasan® or Miglyol 812®), oleic acid or propylene glycol.

The liquid carrier may also comprise a microemulsion. Microemulsions are also well suited as the liquid carrier vehicle. Microemulsions are quaternary systems comprising an aqueous phase, an oily phase, a surfactant and a cosurfactant. They are translucent and isotropic liquids.

Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

The oily phase can in particular be formed from mineral or vegetable oils, from unsaturated polyglycosylated glycerides or from triglycerides, or alternatively from mixtures of such compounds. The oily phase preferably comprises triglycerides and more preferably medium-chain triglycerides, for example $C_8$–$C_{10}$ caprylic/capric triglyceride. The oily phase will represent, in particular, from about 2 to about 15%, more particularly from about 7 to about 10%, preferably from about 8 to about 9%, V/V of the microemulsion.

The aqueous phase includes, for example water or glycol derivatives, such as propylene glycol, glycol ethers, polyethylene glycols or glycerol. Propylene glycol, diethylene glycol monoethyl ether and dipropylene glycol monoethyl ether are especially preferred. Generally, the aqueous phase will represent a proportion from about 1 to about 4% V/V in the micro emulsion.

Surfactants for the microemulsion include diethylene glycol monoethyl ether, dipropyelene glycol monomethyl ether, polyglycolysed $C_8$–$C_{10}$ glycerides or polyglyceryl-6 dioleate. In addition to these surfactants, the cosurfactants include short-chain alcohols, such as ethanol and propanol.

Some compounds are common to the three components discussed above, i.e., aqueous phase, surfactant and cosurfactant. However, it is well within the skill level of the practitioner to use different compounds for each component of the same formulation.

The cosurfactant to surfactant ratio will preferably be from about 1/7 to about 1/2. There will preferably be from about 25 to about 75% V/V of surfactant and from about 10 to about 55% V/V of cosurfactant in the microemulsion.

Likewise, the co-solvents are also well known to a practitioner in the formulation art. Preferred co-solvents are those which is a promoter of drying and include, for example, methanol, absolute ethanol, ethanol, isopropanol (2-propanol) or benzyl alcohol.

The crystallization inhibitor can in particular be present in a proportion of about 1 to about 20% (W/v), preferably of about 2 or about 5 to about 15%. The inhibitor preferably corresponds to the test in which 0.3 ml of a solution comprising 10% (W/V) of the compound of formula (I) in the liquid carrier and 10% of the inhibitor are deposited on a glass slide at 20° C. and allowed to stand for 24 hours. The slide is then observed with the naked eye. Acceptable inhibitors are those whose addition provides for few or no crystals, and in particular less than 10 crystals, preferably 0 crystals.

Although this is not preferred, the formulation can optionally comprise water, in particular in a proportion of 0 to about 30% (volume by volume V/V), in particular of 0 to about 5%.

The formulation can also comprise an antioxidizing agent intended to inhibit oxidation in air, this agent being in particular present in a proportion of about 0.005 to about 1% (W/V), preferably of about 0.01 to about 0.05%.

Crystallization inhibitors which can be used in the invention include:

- polyvinylpyrrolidone, polyvinyl alcohols, polyvidone, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others,
- anionic surfactants, such as alkaline stearates, in particular sodium, potassium or ammonium stearate; calcium stearate or triethanolamine stearate; sodium abietate; alkyl sulphates, in particular sodium lauryl sulphate and sodium cetyl sulphate; sodium dodecylbenzenesulphonate or sodium dioctyl sulphosuccinate; or fatty acids, in particular those derived from coconut oil,
- cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulphate and sulphonate anions; cetyltrimethylammonium bromide is one of the cationic surfactants which can be used,
- amine salts of formula $N^+R'R''R'''$, in which the R radicals are identical or different optionally hydroxylated hydrocarbon radicals; octadecylamine hydrochloride is one of the cationic surfactants which can be used,
- non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethyehated fatty alcohols, polyoxyethylenated fatty acids or copolymers of ethylene oxide and of propylene oxide,
- amphoteric surfactants, such as substituted lauryl compounds of betaine,
- or preferably a mixture of at least two of the compounds listed above.

In a particularly preferred embodiment, a crystallization inhibitor pair will be used. Such pairs include, for example, the combination of a film-forming agent of polymeric type and of a surface-active agent. These agents will be selected in particular from the compounds mentioned above as crystallization inhibitor.

Particularly preferred film-forming agents of polymeric type include:

- the various grades of polyvinylpyrrolidone,
- polyvinyl alcohols, and
- copolymers of vinyl acetate and of vinylpyrrolidone.

Especially preferred surface-active agents, include those made of non-ionic surfactants, preferably polyoxyethylenated esters of sorbitan and in particular the various grades of polysorbate, for example Polysorbate 80.

The film-forming agent and the surface-active agent can in particular be incorporated in similar or identical amounts within the limit of the total amounts of crystallization inhibitor mentioned elsewhere.

The pair thus constituted secures, in a noteworthy way, the objectives of absence of crystallization on the coat and of maintenance of the cosmetic appearance of the fur, that is to say without a tendency towards sticking or towards a sticky appearance, despite the high concentration of active material.

Particularly preferred antioxidizing agents are those conventional in the art and include, for example, butylated hydroxyanisole, butylated hydroxytoluene, ascorbic acid, sodium metabisulphite, propyl gallate, sodium thiosulphate or a mixture of not more than two of them.

The formulation adjuvants discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients or adjuvants are added.

The spot-on and pour-on formulations are deposited onto the skin, this is generally a localized application over a surface area of less than 10 $cm^2$, especially between 5 and 10 $cm^2$, in particular at two points, and preferably localized between the animals shoulders. The volume applied can be of the order of about 0.3 to about 1 ml, preferably of the order of about 0.5 ml, for cats and of the order of about 0.3 to about 3 ml for dogs, depending on the weight of the animal.

EXAMPLES

The invention is further described in the following examples, and, better understanding of the present invention and of its many advantages will be had from the following example, given by way of illustration.

Example 1

A topical formulation having the following composition:

| Ingredients | Function | % |
| --- | --- | --- |
| Eprinomectin | Active | 0.034 w/v |
| Praziquantel | Active | 11.36 w/v |
| Butylatedhydroxy toluene | Antioxidant | 0.01 w/v |
| Povidone K-30 | Thickener | 2.0 w/v |
| Propylene glycol | Solvent | qs 100 v/v | was prepared by dissolving in sequence while stirring the povidone, BHT and eprinomectin in 90 ml of propylene glycol. Next, while stirring, praziquantel was added to the solution and heated until the praziquantel was dissolved. The solution was cooled to room temperature and adjusted to volume with propylene glycol.

Example 2

A topical formulation having the following composition:

| Ingredients | Function | % |
| --- | --- | --- |
| Eprinomectin | Active | 0.030 w/v |
| Praziquantel | Active | 10.0 w/v |
| Butylatedhydroxy toluene | Antioxidant | 0.01 w/v |
| Povidone K-30 | Thickener | 2.0 w/v |
| Glycerol formal | Solvent | 15.0 v/v |
| Propylene glycol | Solvent | qs 100 v/v | was prepared by dissolving in sequence while stirring povidone, BHT and eprinomectin in 15 ml of glycerol formyl and 65 ml of propylene glycol. Next the praziquantel was added to the solution and heated until the praziquantel was dissolved. The solution was cooled to room temperature and the volume was adjusted by adding propylene glycol.

Example 3

A topical formulation having the following composition:

| Ingredients | Function | % |
|---|---|---|
| Eprinomectin | Active | 0.030 w/v |
| Praziquantel | Active | 10.0 w/v |
| Butylatedhydroxy toluene | Antioxidant | 0.01 w/v |
| Povidone K-30 | Thickener | 2.0 w/v |
| Benzyl alcohol | Solvent | 15.0 v/v |
| Propylene glycol | Solvent | qs 100 v/v | was prepared using a process analogous to that of Example 2.

Example 4

A topical formulation having the following composition:

| Ingredients | Function | % |
|---|---|---|
| Eprinomectin | Active | 0.030 w/v |
| Praziquantel | Active | 10.0 w/v |
| Butylatedhydroxy toluene | Antioxidant | 0.01 w/v |
| Povidone K-30 | Thickener | 2.0 w/v |
| Glycerol formal | Solvent | 15.0 v/v |
| Propylene glycol | Solvent | qs 100 v/v | was prepared using a process analogous to that of Example 2.

Example 5

A topical formulation having the following composition:

| Ingredients | Function | % w/v |
|---|---|---|
| Eprinomectin | Active | 0.030 |
| Praziquantel | Active | 10.0 |
| Butylatedhydroxy toluene | Antioxidant | 0.01 |
| Povidone K-30 | Thickener | 2.0 |
| Benzyl alcohol | Solvent | 100 | was prepared using a process analogous to that of Example 1.

Example 6

A topical formulation having the following composition:

| Ingredients | Function | % |
|---|---|---|
| Eprinomectin | Active | 0.030 w/v |
| Praziquantel | Active | 10.0 w/v |
| Butylatedhydroxy toluene | Antioxidant | 0.01 w/v |
| Povidone K-30 | Thickener | 2.0 w/v |
| Glycerol formal | Solvent | qs 100 v/v | was prepared using a process analogous to that of Example 1.

Example 7

A topical formulation having the following composition:

| Ingredients | Function | % w/v |
|---|---|---|
| Eprinomectin | Active | 0.050 |
| Praziquantel | Active | 5.0 |
| Labrafil ® M1944CS | Solvent | 54.1 |
| Isopropanol | Solvent | 38.6 |
| BHA | Antioxidant | 0.01 |
| Dimethylacetamide | Penetration enchancer | 3 |
| Polyvidone (Kollidon ® 17) | Thickener | 2 | is prepared by adding Labrofil® M1994CS, and isopropanol together and mixing the solvent. Next, BHA is added and dissolve, followed by Kollidon® 17. Add prizanquantel and dissolve. Eprinomectin is added, dissolve. Add dimethylacetamide and dilute with ethanol.

Example 8

A topical formulation having the following composition:

| Ingredients | Function | % w/v |
|---|---|---|
| Eprinomectin | Active | 0.030 |
| Praziquantel | Active | 8.5 |
| BHT | Antioxidant | 0.01 |
| Glycerol formal | Solvent | 30 |
| Isopropanol | Solvent | 20 |
| Propylene glycol | Solvent | QS 100 | is prepared at room temperature by adding BHT to the glycerol formal, then dissolving praziquantel and eprinomectin. Next, isopropanol is added and then dilute with propylene glycol.

Example 9

A topical formulation having the following composition:

| Ingredients | Function | % w/v |
|---|---|---|
| Eprinomectin | Active | 0.030 |
| Praziquantel | Active | 6.0 |
| Isopropanol | Solvent | 50 |
| Dimethylacetamide | Solvent | 40 |
| BHA | Antioxidant | 0.01 |
| Polyvidone (Kollidone ® 17 or Kollidone ® VA 640) | Thickener | 20 |
| Isopropanol | Solvent | QS 100 | is prepared by adding BHA and polyvidone to 50 ml of isopropanol and dissolve. The eprinomectin is added and dissolve. Next, 40 ml of dimethylacetamide is added and the praziquantel is added. The solution is then diluted with isopropanol.

Example 10

A topical formulation having the following composition:

| Ingredients | Function | % w/v |
| --- | --- | --- |
| Eprinomectin | Active | 0.030 |
| Praziquantel | Active | 6.0 |
| Miglyol ® 840 | Solvent | 50 |
| Dimethylacteamide | Solvent | 40 |
| BHA | Antioxidant | 0.01 |
| Miglyol ® 840 | Solvent | QS 100 | is prepared by dissolving BHA in 50 ml of Miglyol® 840, then adding eprinomectin with mixing until dissolves. Next, 40 ml of dimethylacetamide is added following the addition of praziquantel and mixing until dissolves. Dilute with Miglyol® to 100 ml.

Example 11

A topical formulation having the following composition:

| Ingredients | Function | % w/v |
| --- | --- | --- |
| Eprinomectin | Active | 0.030 |
| Praziquantel | Active | 10.0 |
| Dimethyl Isosorbide | Solvent | 43 |
| Isopropanol | Solvent | 40 |
| Isopropanol | Solvent | QS 100 | is prepared by dissolving eprinomectin in 40 ml of isopropanol, then adding the dimethyl isosorbide and then praziquantel mix until dissolve and dilute with isopropanol to 100 ml.

Example 12

A topical formulation having the following composition:

| Ingredients | Function | % w/v |
| --- | --- | --- |
| Eprinomectin | Active | 0.030 |
| Praziquantel | Active | 6.0 |
| Dimethyl isosorbide | Solvent | 40 |
| Propylene glycol | Solvent | 40 |
| Propylene glycol | Solvent | QS 100 | is prepared by dissolving eprinomectin in 40 ml of propylene glycol, adding dimethyl isosorbide then praziquantel and mix to dissolve. Dilute with propylene glycol to 100 ml.

Example 13

| Ingredients | Function | % w/v |
| --- | --- | --- |
| Eprinomectin | Active | 0.030 |
| Praziquantel | Active | 10.0% |
| Dimethyl Isosorbide | Solvent | 46% v/v |
| Propylene glycol | Solvent | 40% v/v |
| Propylene glycol | Solvent | QS 100% with propylene glycol | is prepared by dissolving eprinomectin in propylene glycol, adding dimethyl isosorbide then praziquantel, mix until dissolved. Dilute with propylene glycol to 100 ml.

The above description of the invention is intended to be illustrative and not limiting. Various changes or modifications in the embodiment described may occur to those skilled in the art. These can be made without departing from the scope or spirit of the invention.

The invention claimed is:

1. A spot-on composition consisting essentially of:
   a) a pharmaceutically active combination consisting of at least one macrocyclic lactone selected from the group consisting of moxidectin, doramectin, emamectin, abamectin, ivermectin, selamectin and eprinomectin and at least one compound selected from the group consisting of praziquantel, morantel and pyrantel in a topically effective amount;
   b) a thickening agent; and
   c) a liquid carrier vehicle;
   wherein the a liquid carrier vehicle comprises a solvent and a cosolvent wherein the solvent is selected from the group consisting of benzyl alcohol, butyl diglycol, dimethylacetamide, dimethylformamide, dimethyl isosorbide, $C_8$–$C_{10}$ caprylic/capric triglycerides, dipropylene glycol n-butyl ether, ethanol, isopropanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone, diethylene glycol monoethyl ether, ethylene glycol, diethyl phthalate, and a mixture of at least two of these solvents and the cosolvent is selected from the group consisting of methanol, ethanol, absolute ethanol, isopropanol or benzyl alcohol; and the composition further comprises a crystallization inhibitor selected from the group consisting of an anionic surfactant, a cationic surfactant, a non-ionic surfactant, an amine salt, an amphoteric surfactant, polyvinylpyrrolidone, polyvinyl alcohols, copolymers of vinyl acetate and vinylpyrrolidone, polyethylene glycols, benzyl alcohol, mannitol, glycerol, polyvidone, sorbitol, polyoxyethylenated sorbitan esters, lecithin, carboxymethylcellulose, acrylic derivatives, and a mixture of these crystallization inhibitors.

2. The spot-on composition according to claim 1, wherein
   the anionic surfactant is alkaline stearates, sodium abietate, alkyl sulphates, sodium dodecylbenzenesulphonate, sodium dioctylsulphosuccinate, or fatty acids;
   the cationic surfactant is water-soluble quaternary ammonium salts of formula $N^+R'R''R'''R''''Y^-$ in which the radicals R, R', R'', R''', R'''' independently are hydrocarbon radical; optionally hydroxylated, and $Y^-$ is an anion of a strong acid;
   the amine malt is an amine salt of $N^+R'R''R'''$ in which the radicals R, R', R'', R''', R'''' independently are optionally hydroxylated hydrocarbon radicals;

the non-ionic surfactant is optionally substituted polyoxyethylenated sorbitan esters, polyoxyethylenated alkyl ethers, polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide; and the amphoteric surfactant is lauryl-substituted betaine compounds.

3. The spot-on formulation according to claim 1, where the crystallization inhibitor is a crystallization inhibitor system comprising a polymeric film-forming agent and a surfactant.

4. The spot-on formulation according to claim 1, wherein the polymeric film-forming agent is polyvinylpyrrolidone, polyvinyl alcohols, or a copolymer of vinyl acetate and polyvinylpyrrolidone and the surfactant is a non-ionic surfactant.

5. The spot-on formulation according to claim 1, wherein the crystallization inhibitor system is a mixture of polyvinylpyrrolidone and polyoxethylene (20) sorbitan monooleate.

6. A method for increasing the systemic availability of a pharmaceutically active combination consisting of at least one macrocyclic lactone and at least one compounds selected from the group consisting of praziquantel or morantel in an animal which comprises administering a topical formulation according to claim 1 to the animal.

* * * * *